United States Patent [19]

Suzuki et al.

[11] 4,145,764
[45] Mar. 27, 1979

[54] ENDOSSEOUS IMPLANTS

[75] Inventors: Kazuo Suzuki; Hideki Yoshizawa; Michio Ito, all of Shioziri, Japan

[73] Assignees: Sumitomo Chemical Co., Ltd., Osaka; Matsumoto Dental College, Nagano, both of Japan

[21] Appl. No.: 707,716

[22] Filed: Jul. 21, 1976

[30] Foreign Application Priority Data

Jul. 23, 1975 [JP] Japan .................................. 50/90406

[51] Int. Cl.² .......................... A61F 1/24; A61C 13/00
[52] U.S. Cl. ...................................... 3/1.9; 128/92 C; 32/10 A; 427/2; 427/423
[58] Field of Search ................................... 3/1.9-1.913; 128/92 C, 92 CA; 32/10 A

[56] References Cited

U.S. PATENT DOCUMENTS

| | | | |
|---|---|---|---|
| 3,605,123 | 9/1971 | Hahn | 3/1.9 |
| 3,896,547 | 7/1975 | Kulwiec | 32/10 A |
| 3,987,499 | 10/1976 | Scharbach et al. | 3/1.9 X |

FOREIGN PATENT DOCUMENTS 2306552  8/1974  Fed. Rep. of Germany ............. 3/1.91

OTHER PUBLICATIONS

"Development of Ceramic & Ceramic Composite Devices for Maxillofacial Applications" by T. D. Driskell et al., Journal of Biomedical Materials Research Symposium, No. 2, (part 2), 1972, pp. 353 & 354 relied upon.

Primary Examiner—Ronald L. Frinks
Attorney, Agent, or Firm—Birch, Stewart, Kolasch and Birch

[57] ABSTRACT

An improved implant comprising a metallic base material and a coating layer of a ceramics which is formed by thermally sprayed firstly a bonding agent and secondly ceramic powders (optionally containing a porcelain) around the outersurface of the metallic base material. The implant has a sufficient mechanical strength (e.g. impact strength) and hence an excellent break-resistance and further a good affinity to tissues of living bodies and is useful for implantation in various bones including tooth roots and joints in living bodies.

4 Claims, 3 Drawing Figures

U.S. Patent    Mar. 27, 1979    4,145,764
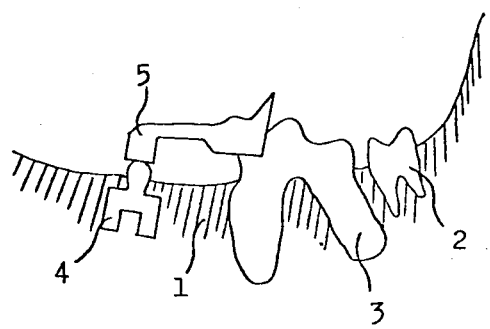
FIG. I
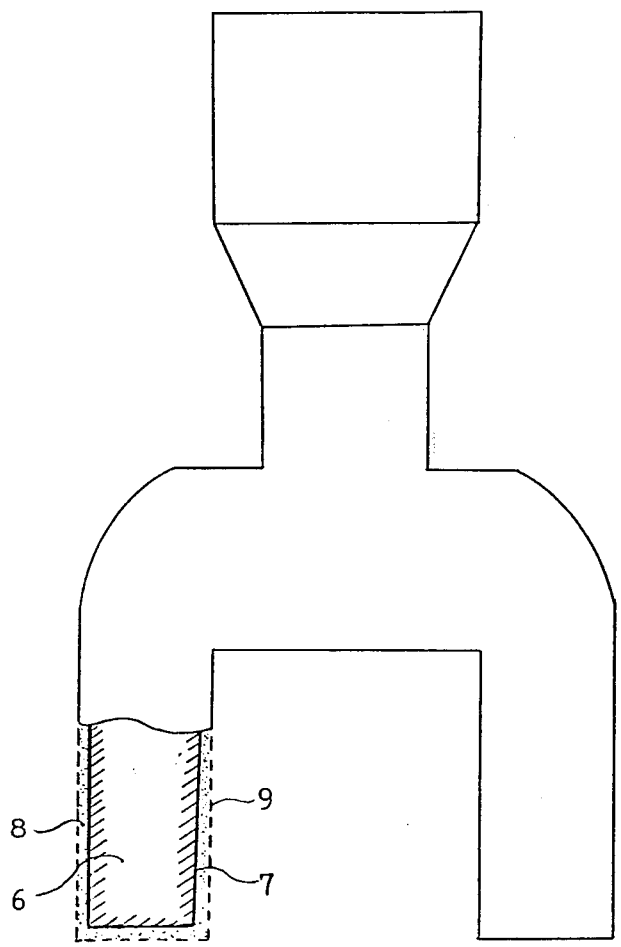
FIG. 2A
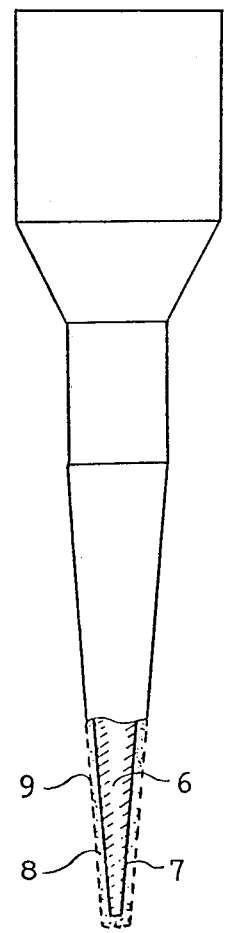
FIG. 2B

ENDOSSEOUS IMPLANTS

BACKGROUND AND SUMMARY OF THE INVENTION

The present invention relates to improvement of implants for bones. More particularly, it relates to an improved implant for a bone, a joint or a tooth root comprising a metallic base material and a coating layer of ceramics which is formed by thermally sprayed ceramic powders around the outersurface of the metallic base material.

The so-called implantology which comprises insertion of artificial materials such as artificial organs, artificial blood vessels, artificial bones and artificial tooth roots into living bodies so as to recover lost parts of living bodies or their functions has been in the limelight in recent years. It is said that a trial of implantation goes back to ancient times. Particularly in these ten-odd years, a huge number of treatments by implantation have been performed on bones and tooth roots to afford good results in the remedy of the defects or recovery of functions thereof. However, an artificial bone or tooth root which can satisfy the necessary requirements as the material for living bodies, i.e. affinity to living bodies, safety and durability, has not yet been obtained.

As metallic materials conventionally used for preparation of artificial bones or tooth roots mainly, cobalt-chromium alloys, stainless steel, titanium and tantalum are exemplified. On the other hand, as ceramic materials, aluminum oxide or carbon materials have been recently considered. Although metallic materials are excellent in mechanical strength, particularly in impact strength, they are faulty in their affinity to tissues of living bodies. For example, when a metallic implant is used, metal ions are dissolved therefrom in living bodies and produce a toxic action to bone cells around the implant. Further, the bone-formation is obstructed probably because of too large a thermal conductivity of the metallic implant. Among the metallic materials, tantalum is particularly superior in corrosion-resistance and hence has been employed as fixing plates for skulls or fractured parts of bones and implants for jawbones since around 1940. The metal is, however, difficult to process. To the contrary, ceramic materials show generally a good affinity to bones, and the bone tissues penetrate into fine pores of the ceramic materials to produce a strong fixation, without reaction between the ceramic material and the tissue. Besides, they are also excellent in durability, that is, they are resistant to corrosion decomposition. But on the other hand, they possess a poor impact strength.

As the results of the present inventors' studies, it has now been found that a desirable implant for bones, joints and tooth roots having a sufficient impact strength and hence an excellent break-resistance while retaining the advantages of ceramic materials abovementioned can be obtained by coating a metallic base material with ceramic powders.

Accordingly, an object of the present invention is to provide an improved implant for a bone, a joint and a tooth having excellent mechanical strength and affinity to living bodies.

Another object of the present invention is to provide a method for improving metallic implants by thermally spraying ceramic powders on the surface of the metallic base material to form a layer of the ceramics.

A further object of the present invention is to provide an improved artificial bones useful as implants for various bones including joints and tooth roots with good durability.

A still further object of the present invention is to provide a method for producing the improved implants.

The implant of the present invention comprises a metallic base material and a coating layer of ceramics which is formed by thermally spraying ceramic powders around the outersurface of the metallic base material.

The present invention will be hereinafter explained in detail with reference to the accompanying drawing, wherein:

FIG. 1 is a schematic view of an embodiment of the implant for the lower jawbone of a dog, wherein 1 represents the lower jawbone, 2 and 3 are natural teeth, 4 is an artificial tooth root and 5 is an artificial tooth crown attached on the artificial tooth root 4, and FIG. 2A is a front schematic view of an embodiment of an implant for a jawbone of blade type according to the present invention, and FIG. 2B is a side view thereof, wherein 6 represents a metallic implant (base material), 7 is a self-bonding type bonding agent and 8 is a ceramic layer containing unopened pores which do not reach the metal surface. According to the present invention, as shown in FIG. 2, a ceramic coating is applied to the surface of a metallic implant material so as to obtain an implant being hardly breakable with a sufficient impact strength and acting to the surrounding bone tissues in a similar manner as ceramic materials.

As the metallic base material in the present invention, there may be employed any conventional one used as artificial materials for bones, joints and tooth roots which does not exhibit harmful influences on living bodies and possesses an appropriate mechanical strength. Specific examples are a cobalt-chromium-nickel alloy, a cobalt-chromium-molybdenum alloy, stainless steel 18-8, 316 L, titanium, tantalum, etc.

In the present invention, a bonding agent is used as a primer for aiding the formation of the coating layer of ceramics on the surface of the metallic base material. The bonding agent may be self-bonding type material which can microscopically bond even onto a smooth non-porous substarate at moderate substrate temperatures, for instance, powders of molybdenum, tantalum, niobium, nickel-chromium-aluminum powdery mixture, nickel-aluminum powdery mixture, or the like.

The ceramics used in the present invention include any conventional thermal spray materials which are usually used for the treatment of the surface of metals by a thermal spray method in order to give them a corrosion resistance, wear resistance or the like, for instance, metal oxides, such as aluminum oxide, zirconium oxide, or titanium oxide which are used alone or in a mixture of two or more thereof.

A porcelain may be applied by baking onto the ceramic layer so that possible opened pores which penetrate through the ceramic layer may be plugged, or it may be incorporated into the ceramics to be thermally sprayed to avoid the formation of such pores.

The procelains used in this invention may be a mixture or a molten mixture which contains predominantly silicon dioxide ($SiO_2$), aluminum oxide ($Al_2O_3$), calcium oxide (CaO), potassium oxide ($K_2O$), sodium oxide ($Na_2O$), Zirconium oxide ($ZrO_2$), titanium oxide ($TiO_2$), barium oxide (BaO), boron trioxide ($B_2O_3$), stannic oxide ($SnO_2$), or the like. Suitable examples of the porcelains are the commercially available porcelains (e.g. Opaque, Dentin, Enamel, Translucent) for fusing onto dental metal crowns.

In the former method, these porcelains are preferably glazed onto the whole surface of the ceramic layer in such a thickness that the original surface unevenness is not lost. In the latter case, about 3–50 parts (preferably 5–20 parts) by weight of the porcelain may be incorporated into 100 parts by weight of the ceramics.

The implant of this invention may be applied to various organs of living bodies. For example, it may be implanted into a tooth, a bone, a mucous membrane, behind periosteum or the like as a substitute or a supplement for a bone, a joint or a tooth. For this purpose, the implant of this invention may optionally be shaped according to the present invention.

In present invention, any shape of a metallic base material may be used. For example, it can be in the shape like a pin, a screw, a blade, an anchor, a plate or a mesh.

According to the present invention, the preparation of implants is effected in the following manner: a metallic material is subjected to molding, calcination or cutting processing, preferably casting, and then to polishing to obtain a base material, which is grit-blasted, and thereafter, to the outersurface of the metallic base material thus treated is applied (1) the bonding agent and (2) the ceramics (optionally, containing a porcelain), in order, by using a commercially available thermal spray apparatus (i.e. by blowing and laminating thereon the bonding agent and the ceramics molten or nearly molten by a technique of combustion or with electric energy), preferably by using a thermal plasma spray apparatus (i.e. by applying the bonding agent and the ceramics in the form of a plasma jet of a supersonic electromagnetic liquid having a high temperature obtained by arcing). The portion which is not coated with the ceramics is previously masked by applying a marking ink, an aluminum adhesive tape or other appropriate means prior to subjecting it to grit blasting. For some specific uses of these implants, for instance, in case of artificial joints, a considerable degree of smoothness is required on the ceramic layer surface. In such cases, application of porcelain material and subsequent baking thereof in a vacuum furnace are repeated to obtain an artificial bone with the desired smoothness. As a matter of course, the baking in a vacuum furnace is effected also in case of the porcelain being not applied. The baking temperature is 1000° C. When the application of the porcelain material is effected, rapid heating and rapid cooling are desired for preventing the deformation due to the sag of the porcelain on baking or reducing the deformation as much as possible.

The thickness of the bonding layer and that of the ceramic layer which optionally contains the porcelain are not particularly limited, but preferred bonding layer may be about 500μ or less (particularly 50–150μ) in thickness and preferred ceramic layer may be about 2,000μ or less (particularly 50–1,000μ) in thickness.

The present invention is illustrated by the following Examples but is not limited thereto.

EXAMPLE 1

Using a cobalt-chromium-nickel alloy ("Nobilium" manufactured by Nobilium), a base material for an implant for bone was prepared in the following manner. The cobalt-chromium-nickel alloy was subjected to high frequency melting and then to centrifugal casting, and the casted product was polished to obtain a base material for an implant for bone (weight, 0.7 g).

The metallic base material for implant was grit-blasted by the aid of a blast apparatus (a mammoth type ventiblast apparatus manufactured by Metco Inc., England; blasting agent, Metcolite VF, trade name of Metco Inc.; pressure, 30 psi). Then, under generation of argon-hydrogen-plasma jet flame (ARC electric current 500 Amp) by the aid of a plasma spray apparatus (6MM-630 type, manufactured by Metco Inc., equipped with an electric powder supplier). nickel-aluminum composite powders as a self-bonding type bonding agent (Metco powder No. 450 manufactured by Metco Inc.) were thermally sprayed to form a coating layer having a thickness of about 80 μ as the first layer on the whole outersurface of the base material, and mixed powders of 90% by weight of aluminum oxide (Metco powder No. 105 manufactured by Metco Inc.) and 10 % by weight of dentin porcelain ("VMK 68–549" manufactured by VITA Co.) were then thermally sprayed to form the second layer of about 200 μ in average thickness.

The product was rapidly heated to 1000° C. in a vacuum furnace and immediately cooled with rapidity. The dentin porcelain was again applied to the product, and the baking was effected under the same condition to obtain the desired implant for bone. The thus prepared implant was embedded into a tibia of a pig, and observation by X-ray fluoroscopy was effected for 2 months thereafter, whereby formation of dense bone was confirmed around the implant.

EXAMPLE 2

Using the same cobalt-chromium-nickel alloy as used in Example 1, a test piece (weight, 0.7 g) was prepared in the same manner as described in Example 1. The obtained test piece was grit-blasted only on one surface as in Example 1, and then plasma spray was effected to form a layer of nickel-aluminum powders having a thickness of about 80 μ and a layer of a mixture of 90% by weight of aluminum oxide and 10% by weight of dentin porcelain having a thickness of about 200 μ, followed by baking thereof at 1000° C. Then, the dentin porcelain was applied thereto uniformly to obtain a layer of about 100 μ in thickness, and the baking in a vacuum furnace at 1000° C. was effected as in Example 1 to afford the desired implant.

The thus obtained implant shows a bending strength of 8.2 kg/mm$^2$ when determined by the aid of Autograph IS-1500 (manufactured by Shimadzu Seisakusho Ltd). In case of a gold alloy (KIK, manufactured by Ishifuku Kinzoku K. K. ) conventionally employed for a porcelain fused to metal crown, a bending strength of about 8.0 kg/mm$^2$ is reported.

It is therefore thinkable that the product obtained by fusing a porcelain to the cobalt-chromium-nickel alloy according to the invention possesses a sufficient strength for the use in the oral cavity.

EXAMPLE 3

Using a titanium alloy as the base material, an implant for jawbone with coated surface was prepared in the same manner as in Example 1 (shown in FIG. 2 weight : 0.4 (g). The product was embedded into the lower jawbone of a dog, and observation by X-ray fluoroscopy was effected for 4 months thereafter, whereby bone-formation was clearly confirmed around the implant. By macroscopic observation, no abnormal state was observed in the paradental tissues.

According to the present invention, as understood from the above description, since a plasma sprayed layer of ceramics is formed on the surface of a metallic implant material as the base material of an artificial bone, there can be obtained the desired artificial bones improved in the fragility of a ceramic implant, with retaining the mechanical strength of the metal and having the same affinity to the bone tissues as in ceramics.

What is claimed is:

1. A prosthetic article comprising a ceramic coating layer bonded to a metal base by a plasma sprayed layer of a bonding agent applied to the metal base, said ceramic coating layer being formed onto the metal base by plasma spraying method with an uneven surface, said ceramic coating layer containing a plurality of pores therein and being a member selected from the group consisting of aluminum oxide, zirconium oxide, titanium oxide, and a mixture thereof, and the metal base is made of a material selected from the group consisting of cobalt-chromium-nickel alloy, cobalt-chromium-molybdenum alloy, stainless steel 18-8, stainless steel 316L, titanium and tantalum, and said bonding agent being selected from the group consisting of molybdenum powder, tantalum powder, niobium powder, nickel-chromium-aluminum powdery mixture and nickel-aluminum powdery mixture.

2. The prosthetic article according to claim 1, wherein the ceramic coating layer contains porcelain which predominantly contains silicon dioxide, aluminum oxide, calcium oxide, potassium oxide, sodium oxide, zirconium oxide, titanium oxide, barium oxide, boron trioxide and stannic oxide.

3. The prosthetic article according to claim 1, which further contains a baked layer of porcelain on the layer of ceramics, said porcelain layer predominantly containing a member selected from the group consisting of silicon dioxide, aluminum oxide, calcium oxide, potassium oxide, sodium oxide, zirconium oxide, titanium oxide, barium oxide, boron trioxide, and stannic oxide.

4. The prosthetic article according to claim 2, which further contains a baked layer of porcelain on the layer of ceramics, said procelain layer predominantly containing a member selected from the group consisting of silicon dioxide, aluminum oxide, calcium oxide, potassium oxide, sodium oxide, zirconium oxide, titanium oxide, barium oxide, boron trioxide, and stannic oxide.

* * * * *